US012629344B2

(12) United States Patent
Prinz et al.

(10) Patent No.: US 12,629,344 B2
(45) Date of Patent: May 19, 2026

(54) TTS-FORMULATION WITH THC

(71) Applicant: LTS LOHMANN THERAPIE-SYSTEME AG, Andernach (DE)

(72) Inventors: Eva-Marie Prinz, Weißenthurm (DE); Marco Emgenbroich, Rheinbach (DE); Birgit Braun, Wied (DE); Peter Bohnenkämper, Horhausen (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 246 days.

(21) Appl. No.: 18/277,679

(22) PCT Filed: Feb. 17, 2022

(86) PCT No.: PCT/EP2022/053998
§ 371 (c)(1),
(2) Date: Aug. 17, 2023

(87) PCT Pub. No.: WO2022/175408
PCT Pub. Date: Aug. 25, 2022

(65) Prior Publication Data
US 2024/0130978 A1 Apr. 25, 2024
US 2024/0226029 A9 Jul. 11, 2024

(30) Foreign Application Priority Data

Feb. 18, 2021 (EP) ..................................... 21157938

(51) Int. Cl.
A61K 47/10 (2017.01)
A61K 9/70 (2006.01)
(Continued)

(52) U.S. Cl.
CPC .......... A61K 9/7084 (2013.01); A61K 31/658 (2023.05); A61K 47/10 (2013.01);
(Continued)

(58) Field of Classification Search
CPC .... A61K 9/7084; A61K 31/658; A61K 47/10; A61K 47/14; A61K 47/32; A61K 47/34
See application file for complete search history.

(56) References Cited

U.S. PATENT DOCUMENTS 6,328,992 B1 * 12/2001 Brooke ..................... A61P 1/14
424/443
8,435,556 B2 * 5/2013 Stinchcomb ............ A61P 25/00
424/443
(Continued)

FOREIGN PATENT DOCUMENTS

JP 2023-533900 A 8/2023
WO 2021067806 A1 4/2021

OTHER PUBLICATIONS

International Search Report for PCT/EP2022/053998, dated Apr. 25, 2022, 2 pages.
(Continued)

*Primary Examiner* — Guy K Townsend
(74) *Attorney, Agent, or Firm* — Lippes Mathias LLP

(57) ABSTRACT

Disclosed is a transdermal therapeutic system comprising an active agent impermeable backing layer, at least one adhesive layer comprising at least 70% by weight of at least one polysiloxane polymer, at least one tetrahydrocannabinol (THC) and at least one solubilizer, and optionally a protective layer for removal before use, a method for its preparation and its use as a medicament.

15 Claims, 2 Drawing Sheets

(51) Int. Cl.

| | |
|---|---|
| *A61K 31/00* | (2006.01) |
| *A61K 47/14* | (2017.01) |
| *A61K 47/32* | (2006.01) |
| *A61K 47/34* | (2017.01) |

(52) U.S. Cl.
CPC .............. *A61K 47/14* (2013.01); *A61K 47/32* (2013.01); *A61K 47/34* (2013.01)

(56) References Cited

U.S. PATENT DOCUMENTS

| | | | | |
|---|---|---|---|---|
| 8,449,908 | B2 * | 5/2013 | Stinchcomb ........... | A61K 47/12 424/443 |
| 9,044,390 | B1 * | 6/2015 | Speier ................... | A61K 9/006 |
| 10,272,125 | B2 * | 4/2019 | Weimann ............. | A61K 9/7084 |
| 10,821,084 | B2 * | 11/2020 | Weimann .................. | A61P 5/24 |
| 2005/0266061 | A1 * | 12/2005 | Stinchcomb ......... | A61K 31/353 424/448 |
| 2006/0257463 | A1 * | 11/2006 | Elsohly .............. | A61K 36/3482 424/774 |
| 2009/0291128 | A1 * | 11/2009 | Stinchcomb ......... | A61K 9/7084 424/449 |
| 2011/0052694 | A1 * | 3/2011 | Stinchcomb ........... | A61P 17/02 514/420 |
| 2011/0245288 | A1 * | 10/2011 | Stinchcomb .............. | A61P 3/04 514/282 |
| 2016/0022627 | A2 * | 1/2016 | Smith .................. | A61K 9/0014 424/449 |
| 2016/0279073 | A1 * | 9/2016 | Donsky ..................... | A23L 2/52 |
| 2017/0020941 | A1 * | 1/2017 | Naheed .................. | A61K 47/36 |
| 2017/0020942 | A1 * | 1/2017 | Naheed .............. | A61K 36/185 |
| 2017/0021025 | A1 * | 1/2017 | Naheed .................. | A61K 47/36 |
| 2017/0021026 | A1 * | 1/2017 | Naheed ............. | A61K 36/3482 |
| 2017/0071870 | A1 | 3/2017 | Weimann | |
| 2018/0078512 | A1 * | 3/2018 | Weimann ............. | A61K 31/658 |
| 2019/0110981 | A1 * | 4/2019 | Weimann ............. | A61K 31/352 |
| 2019/0231711 | A1 * | 8/2019 | Weimann ............... | A61K 36/71 |
| 2021/0228497 | A1 * | 7/2021 | Weimann ............... | A61K 31/05 |
| 2022/0331479 | A1 * | 10/2022 | Cahill ..................... | A61L 15/44 |
| 2024/0130978 | A1 * | 4/2024 | Prinz .................... | A61K 31/658 |

OTHER PUBLICATIONS

International Preliminary Report on Patentability for PCT/EP2022/053998, mailed Jun. 2, 2023, 14 pages.
Written Opinion of the International Preliminary Examining Authority for PCT/EP2022/053998, mailed Feb. 9, 2023, 6 pages.
Office Action for Japanese Patent Application No. 2023-549827, mailed Jul. 15, 2025, 15 pages.

* cited by examiner

TTS-FORMULATION WITH THC

The present invention relates to a transdermal therapeutic system on the basis of a polysiloxan polymer comprising at least one active agent selected from the group of cannabinoids, a method for its preparation and its use as a medicament.

Transdermal therapeutic systems (TTS) are drug delivery systems that are applied directly to the skin. The active agent is released into the skin and distributed through the body via the bloodstream. Transdermal therapeutic systems are widely known for the application of manifold different active agents. However, the application of active agents via the skin often suffers from poor resorption of the active agents, which has led to only a limited number of commercially successful drugs which are administered via the transdermal route.

With the exception of a few special forms, a TTS can basically be differentiated into two different types, namely those known as matrix systems and those known as reservoir systems. In matrix systems in the simplest case the active agent is dissolved in a self-adhesive layer or may be suspended or dispersed in the adhesive in the form of crystals. In reservoir systems there is usually a compartment which is filled with the active agent in liquid form, and wherefrom the active agent is released into the skin via a permeable membrane, which may be modified with an adhesive layer for adhesion to the skin.

Liquid microreservoir TTS represent a mixture of the two basic forms in that, like in reservoir systems, the active agent is present in the liquid form, which however, as in the matrix system, is distributed throughout the matrix in the form of small active agent droplets.

This has the effect that in liquid microreservoir TTS the active agent is located for the most part not in the polymeric constituents of the system, but in liquid microreservoirs, which are embedded into one or more matrix polymer layers. In their simplest case, the liquid microreservoirs are embedded into a self-adhesive polymer layer.

Concerning its external appearance, a liquid microreservoir TTS designed in this way is not distinguishable from a customary matrix system. However, when investigated under the microscope, the microreservoirs and thus the heterogeneous structure of the adhesive layer become apparent.

Microreservoir TTS are also possible with polymeric matrix systems, which in themselves are not or not sufficiently self-adhesive. In such systems, the lack of adhesiveness can e.g. be compensated by a further self-adhesive layer applied on the matrix layer, which serves to anchor the system on the skin. Similarly, an adhesive can be used to improve adherence of the backing layer to the matrix system comprising the active agent.

Since the negative attitude towards cannabinoids as drugs has changed in recent years and active agents in the form of cannabinoids have been officially approved as medicaments, there is a growing demand for drug delivery systems for the administration of cannabinoids as active agents.

Cannabinoids are rapidly metabolized in the body, so that the concentration level of the active agent in the bloodstream decreases rapidly if cannabinoids are administered via conventional routes. This makes cannabinoids a promising candidate for transdermal applications which allows a precise dose of active agent to be administered over an extended period of time, thereby allowing the concentration levels of the chemical in the bloodstream to remain relatively steady. A difficulty with cannabinoids is on the other hand, that they are highly liphophilic and exhibit a strong tendency to bind to tissue and protein, making transdermal application difficult.

U.S. Pat. No. 10,272,125 B2 describes systems for the transdermal delivery of cannabidiol (CBD), which comprise a membrane or which have a monolithic design. For the latter, cannabidiol was admixed with polyisobutylene, an acrylic adhesive or a silicone adhesive to provide the active ingredient containing layer.

It was the objective of the present invention to provide a stable TTS formulation for the application of tetrahydrocannabinol as a cannabinoid active agent. The TTS formulation should, in spite of the rather disadvantageous properties of the tetrahydrocannabinol (i.e. high hydrophobicity), provide a stable and continuous drug flux through the skin of the patient over a prolonged period of time, preferably for a time period of up to 7 days.

Surprisingly it has now been found that a TTS-formulation according to claim 1, in particular a transdermal therapeutic system comprising i) an active agent impermeable backing layer, ii) at least one adhesive layer comprising at least 70% by weight of at least one polysiloxane polymer, at least one tetrahydrocannabinol (THC) and at least one solubilizer, and optionally iii) a removable protective layer, solves the above mentioned objective.

The inventive transdermal therapeutic system thus comprises i) an active agent impermeable backing layer, ii) at least one adhesive layer comprising at least 70% by weight of at least one polysiloxane polymer, at least one tetrahydrocannabinol and at least one solubilizer and optionally iii) a protective layer, which can be removed before use.

DETAILED DESCRIPTION OF THE INVENTION

Figure 1:
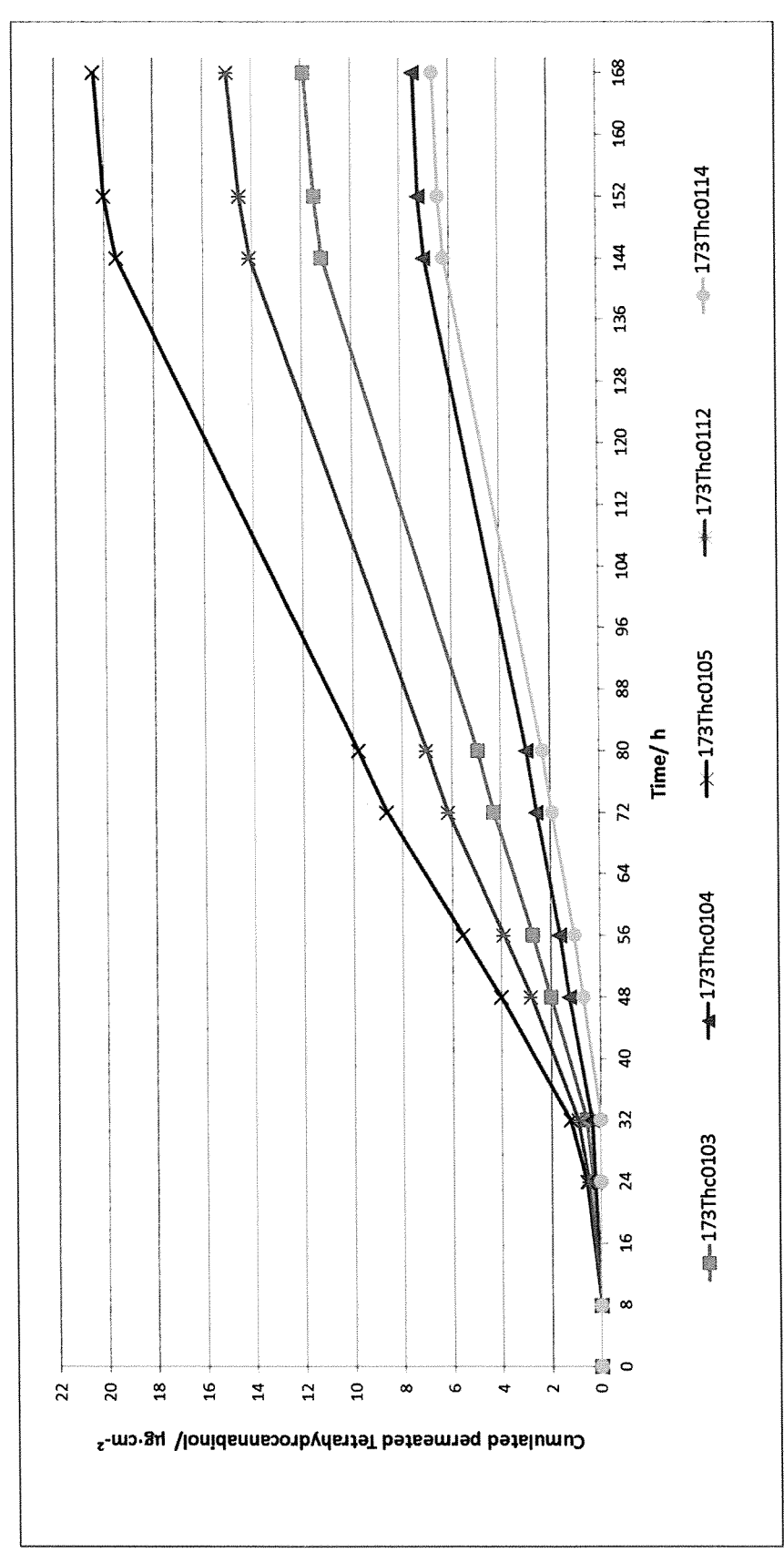
FIG. 1 is the graphical representation of cumulated permeated active agent after 168 hours.

In the context of the present invention, the terms "transdermal therapeutic system" and "TTS" are used interchangeably.

In the transdermal therapeutic system, the polysiloxane polymer forms a matrix, into which the tetrahydrocannabinol is incorporated. In a preferred embodiment, the tetrahydrocannabinol is sufficiently insoluble in the polysiloxane polymer so that upon formation of the transdermal therapeutic system the polysiloxane polymer and the tetrahydrocannabinol segregate at least to some extent to form a microreservoir TTS as described above. In such a microreservoir system, the tetrahydrocannabinol is present predominantly (i.e. at least 60 wt.-%, in particular at least 75 wt.-%, preferably at least 90 wt.-%, and most preferably at least 95 wt.-%) in the microreservoirs formed in the polysiloxane polymer.

As indicated above, the transdermal therapeutic system of the present invention as a first constituent comprises an active agent impermeable backing layer. Suitable materials for the backing layer include films of, for example, polyethylene, polypropylene, polyesters such as polyethylene terephthalate, a copolymer of ethylene and vinyl acetate (EVA), and polyvinyl chloride. Such films may also consist of laminates of different polymers and may further include color layers and/or color pigments. Films of this kind are well known to the person skilled in the art and the best film for the particular purpose can be found without problems.

The transdermal therapeutic system according to the present invention further comprises at least one adhesive layer comprising at least 70% by weight, preferably at least 75% by weight, more preferably at least 80% by weight of at least one polysiloxane polymer. The maximum amount of the polysiloxane polymer is not particularly limited except that it must allow for the presence of effective amounts of the tetrahydrocannabinol and the solubilizer in the adhesive layer. As a suitable maximum amount of the polysiloxane polymer an amount of up to 95% by weight, preferable up to 90% by weight and most preferably up to 86% by weight can be mentioned.

The polysiloxane polymer of the TTS according to the present invention is preferably an amine-resistant polysiloxane polymer. This means that the polysiloxane has no free silanol groups (Si—OH), which in the presence of basic active agents are able to participate in further condensation reactions.

Suitable polysiloxane polymers are polycondensation products of silanol endblocked polydimethylsiloxanes with soluble silicate resins such as those which are commercially available from Dow Corning under the tradename BIO-PSA®. These polysiloxanes are regularly supplied as solutions in various solvents. For the purpose of preparing the TTS of the invention, solutions in low-boiling alkanes, especially n-heptane or ethylacetate, have been found particularly suitable.

Particularly suitable standard silicone adhesives or amine-compatible silicone adhesive like BIO-PSA® polymers comprise BIO-PSA 4101, BIO-PSA 4201, BIO-PSA 4301, BIO-PSA 4102, BIO-PSA 4202, BIO-PSA 4302, BIO-PSA 4401, BIO-PSA 4402, BIO-PSA 4501 and BIO-PSA 4502 (all from Dow Corning).

Moreover, the polysiloxane polymer of the TTS according to the present invention is preferably self-adhesive. This has the advantage that no further adhesive needs to be applied in order to adhere the TTS onto the skin of a patient and also no further adhesive needs to be applied to adhere the adhesive layer onto the active agent impermeable backing layer. Polysiloxanes are usually of only limited miscibility with tackifying additives. Nevertheless, it may be of advantage in an individual case to improve the tack by adding small amounts of tackifiers such as polyterpenes, rosin derivatives, or silicone oils.

The adhesive layer can comprise a single polysiloxane polymer or may comprise a mixture of more than one polysiloxane polymer. As a mixture allows for a more accurate fine-tuning of the final properties, it is preferred that the adhesive layer comprises a mixture of polysiloxane polymers, in particular, a mixture of two polysiloxane polymers. In that case, the ratio of the two polysiloxan polymers is preferably in the range of 1:9 to 9:1, more preferably in the range of 2:8 to 8:2.

In an especially preferred embodiment of the present invention, the adhesive layer comprises a mixture of a high-tack and a medium or low-tack silicone adhesive. The tackiness of silicone polymer depends on the resin-to-polymer ratio, i.e. the ratio of the silanol endblocked polydimethylsiloxane to the silicate resin, which is preferably in the range of from 70:30 to 50:50, more preferably from 65:35 to 55:45. The tackiness increases with increasing amounts of the polymer relative to the resin. High tack silicone polymers are herein designated as those having a resin-to-polymer ratio of up to 57:43, preferably about 55:45, medium tack silicone polymers have a resin-topolymer ratio of more than 57:43 to 63:37, preferably about 60:40, and low tack silicone polymers have a resin-to-polymer ratio of more than 63:37, preferably about 65:35. High tack amine-compatible silicone polymers preferably have a complex viscosity at 0.01 rad/s and 30° C. of about $5 \times 10^6$ Poise, medium tack amine-compatible silicone polymers preferably have a complex viscosity at 0.01 rad/s and 30° C. of about $5 \times 10^8$ Poise, and low tack amine-compatible silicone polymers preferably have a complex viscosity at 0.01 rad/s and 30° C. of about $5 \times 10^9$ Poise.

Most preferably, the adhesive layer comprises a mixture of a medium tack silicone polymer and a high tack silicone polymer, in particular a medium and a high tack amine-compatible silicone polymer, in a ratio of 1:9 to 9:1, preferably in a ratio of 2:8 to 8:2, most preferably in a mixture of 3:7 to 7:3.

Polysiloxanes have low solvency for active agents. This has the consequence that in the absence of additives the active agents in polysiloxanes are present predominantly only in dispersion and not in solution in the polymer.

The transdermal therapeutic system according to the present invention further comprises at least one tetrahydrocannabinol as the active agent.

In the inventive transdermal therapeutic system the tetrahydrocannabinol can be natural, but can also be a partly or fully synthetic. E.g., as a fully synthetic tetrahydrocannabinol, R-(6a,10a)-Δ9-tetrahydrocannabinol is suitable for administration in the transdermal therapeutic system of the present invention.

*Cannabis* extracts and *cannabis* oils, in particular extracts and oils of *Cannabis sativa* or *Cannabis indica*, can similarly be used as the active agent in the transdermal therapeutic system of the present invention. *Cannabis* extracts or oils contain as pharmacologically active agents, among others tetrahydrocannabinol (predominantly Δ9-tetrahydrocannabinol, to a lesser extent Δ8-tetrahydrocannabinol).

The TTS according to the present invention comprises at least one tetrahydrocannabinol (THC) selected from the group comprising Δ8-tetrahydrocannabinol, Δ9-tetrahydrocannabinol and R-(6a,10a)-Δ9-tetrahydrocannabinol, but does not encompass any prodrugs, derivatives and analogs of THC.

The amount of the at least one tetrahydrocannabinol in the TTS according to the present invention is preferably from 0.1 to 20% by weight, more preferably from 1 to 15% by weight, and most preferably from 3 to 10% by weight based on the total weight of the at least one adhesive layer.

As a third component of the adhesive layer, the inventive transdermal therapeutic system comprises at least one solubilizer. A solubilizer (or solubilizing agent) in the context of the present invention is a substance which contributes to and facilitates the dissolution of the tetrahydrocannabinol in the polymer.

Suitable solubilizers for use in the present invention include saturated or unsaturated fatty acids or fatty acid esters such as pentanoic acid, capric acid, caprylic acid, myristic acid, palmitic acid, stearic acid, arachidic acid, behenic acid, linoleic acid, lignoceric acid, isoverlic acid, neoheptonic acid, neonanonic acid, isostearic acid, pentanoic acid, hexanoic acid, ricinoleic acid, octanoic acid, nonanoic acid, decanoic acid, lauric acid, Oleic acid, arachidonic acid, galloleic acid, erucic acid, methyl valerate, diethyl sebacitate, methyl laurate, ethyl oleate, isopropyl decanoate, isobutanoic acid, isobutanoic acid, isopropyl myristate, isopropyl palmitate and/or isopropyloleinate. From among these, amphiphilic molecules, i.e. molecule having a twofold amphilicity and containing both a hydrophilic and a lipophilic portion, are preferred. Amphiphilic molecules are in particular the acids mentioned above. Isopropyl myristate and lauric acid are most preferred.

Other suitable solubilizers comprise polyethylene glycol monolaureate (e.g. commercially available under the tradename Lauroglycol 90), polyethylene glycol dodecyl ether/polyoxyethylene(4)lauryl ether (e.g. commercially available under the tradename Brij L4), polyoxyethylen (2) cetyl ether (e.g. commercially available under the tradename Brij C2), PEG-6 mono- and diesters of oleic acid (commercially available in admixture with mono-, di- and triglycerides e.g. under the tradename Labrafil® M 1944 CS), glycerol monooleate (e.g. commercially available under the tradename Citrol™ GMO HP.

In a preferred embodiment, fatty acids (i.e. C2 to C20 saturated or unsaturated aliphatic carboxylic acids), polyethylenglycol, isopropyl myristate and isopropyl palmitate are excluded as solubilizers in the transdermal therapeutic system of the present invention.

The inventors of the present invention have found that also certain polymers provide suitable properties as solubilizers. Polymers which have proven advantageous as solubilizers include e.g. polyvinylpyrrolidone such as polyvinylpyrrolidone 30 (Mw of 40.000) and polyvinyl caprolactame-/polyvinylacetate-/polyethylene glycol-copolymer (e.g. commercially available under the tradename "Soluplus").

In a preferred embodiment, the TTS according to the present invention is characterized in that the at least one solubilizer is a polymer or an amphiphilic molecule which has an HLB of less than 6. The HLB value (HLB=hydrophilic-lipophilic balance=hydro-lipophilic ratio) is a measure of the water or oil solubility of predominantly nonionic surfactants and the stability of emulsions.

The HLB value can be calculated using the following equation:

$$HLB = 20 \times \left(1 - \frac{M_l}{M}\right),$$

wherein $M_l$ is the molar mass of the lipophilic portion of a molecule and M is the molar mass of the entire molecule. The factor 20 is a freely chosen scaling factor, resulting in a scale of 0 to 20.

An HLB value of 1 indicates a lipophilic compound, whereas a chemical compound having an HLB value of 20 has a high hydrophilic content. A value between 3 and 8 is assigned to water-in-oil (w/o) solubilizers/emulsifiers and a value between 8 and 18 oil-in-water (o/w) solubilizers/emulsifiers.

Particularly preferred solubilizers in the inventive TTS are selected from the group comprising polyvinylpyrrolidone 30, lauric acid, caprylic acid, PEG-6 mono- and diesters of oleic acid, polyethylene glycol dodecyl ether/polyoxyethylene(4)lauryl ether, and polyvinylcaprolactam-/polyvinylacetate-/polyethyleneglycol-copolymer.

The amount of the at least one solubilizer in the TTS according to the present invention is preferably in the range of 0.1 to 12% by weight, more preferably in the range of 0.5 to 10% by weight, based on the total weight of the at least one adhesive layer.

The TTS according to the present invention further preferably comprises at least one permeation enhancer. A permeation enhancer, as this term is used in the present invention, is a compound which facilitates the transfer of the active agent through the skin. As a permeation enhancer any compound which is known to the skilled practitioner to have the required properties can be used. Preferred permeation enhancers in the context of the present invention are e.g. propylene glycol, Dipropylene glycol, or 2-(2-ethoxyethoxy)ethanol (commercially available as "Transcutol").

Also some of the solubilizers mentioned above have suitable properties as permeation enhancers such as e.g. PEG-6 mono- and diesters of oleic acid (commercially available in admixture with mono-, di- and triglycerides e.g. under the tradename Labrafil® M 1944 CS) or glycerol monooleate (e.g. commercially available under the tradename Cithrol™ GMO HP or polyethylene glycol monolaureate (e.g. commercially available under the tradename Lauroglycol 90), Thus, in one embodiment, the compounds of the solubilizer and the permeation enhancer may be identical.

The amount of the at least one permeation enhancer ranges preferably from 0.1 to 20% by weight, more preferably from 1 to 15% by weight, most preferably from 2 to 10% by weight based on the total weight of the at least one adhesive layer.

In a preferred embodiment the inventive TTS does not comprise DMSO, which is frequently employed as a permeation enhancer in transdermal therapeutic systems. DMSO in the body is to some extent metabolized to dimethylsulfide which has an unpleasant odor even in very low concentrations. Moreover, according to the present invention it is preferred that the adhesive layer does not comprise a permeation enhancer selected from the group consisting of terpenes, such as cineole.

In the present invention it has further been found that it is not necessary to incorporate a compound into the TTS, which has an HLB-value of 6 or more (as calculated according to the method of Davies). Therefore, in one embodiment, the inventive adhesive layer is substantially devoid (i.e. contain less than 1 wt.-%, preferably less than 0.5 wt.-% and more preferably less than 0.1 wt.-%) of compounds having an HLB of 6 or more. Most preferably, the adhesive layer contains no compounds having an HLB of 6 which are intentionally added.

The TTS according to the present invention further preferably comprises at least one antioxidant. An antioxidant is a chemical compound which prevents or reduces undesired oxidation of other substances, especially of the active agent, which is mainly caused by oxygen and therefore counteracts aging of the TTS. Preferred antioxidants in the practice of the invention are e.g. tocopherol (vitamin E), ascorbyl palmiate, ascorbic acid, or butylhydroxytoluol.

The at least one antioxidant is preferably present in an amount of 0.005 to 2% by weight, preferably from 0.01 to 0.7% by weight based on the total weight of the adhesive layer.

The transdermal therapeutic system according to the present invention further optionally comprises a protective layer for removal before use. Suitable materials for the removable protective layer are, especially for silicone adhesives, polyethylene terephthalate films. The use of such a protective layer for removal before use has the advantage that the packaging and storage of the TTS according to the present invention can be simplified.

In a preferred embodiment the TTS according to the present invention is a microreservoir TTS, wherein the maximum size of the microreservoirs does not exceed 80% of the thickness of the adhesive layer. In a further preferred embodiment the TTS according to the present invention is a microreservoir, wherein the microreservoirs have an average diameter of 5 to 50 μm, preferably of 5 to 35 μm (determined by microscopic observation).

In another preferred embodiment the TTS according to the present invention is a monolithic TTS, wherein the active ingredient (THC) is incorporated in the layer which in use is attached directly to the skin (i.e. this layer contains a least 70 wt.-% and preferably at least 90 wt.-% of the THC in the TTS).

The TTS according to the present invention might further comprise conventional auxiliary additives, like solvents, crystallization inhibitors, viscosity regulating agents, pH regulators, fillers, dyes, gelling agent or any combinations thereof.

The TTS according to the present invention regularly is characterized in that the adhesive layer has a weight of 20 to 300 g/m². Preferably, the adhesive layer has a weight in the range of 50 to 250 g/m², most preferably in the range of 100 to 200 g/m².

The typical size of the adhesive layer in the TTS according to the present invention is 1 to 150 cm² and preferably 5 to 80 cm².

Moreover, the TTS according to the present invention preferably comprises a total amount of active agent of 1 to 120 mg, preferably 5 to 100 mg, more preferably 8 to 90 mg and even more preferably 10 to 60 mg.

In a further aspect, the present invention pertains to a method for preparing a transdermal therapeutic system as described above, which comprises the steps of:
   a) preparing a mixture comprising at least one polysiloxane polymer, at least one active agent selected from the group of tetrahydrocannabinols and at least one solubilizer;
   b) applying the mixture of a) on a protective layer for removal before use, and
   c) applying an active agent impermeable backing layer on the layer of the mixture prepared in step b).

The mixture, which is prepared in step a), preferably comprises a suitable solvent, which dissolves the at least one active agent and the at least one solubilizer in order to allow for a uniform distribution of the active agent in the polysiloxane polymer. If the mixture in step a) contains a solvent, it is preferred that at least at part of the solvent is removed or evaporated, before the active agent impermeable backing layer is applied in step c).

In a yet further aspect, the present invention relates to a TTS obtainable by the aforementioned method.

In a yet further aspect, the present invention relates to the use of a TTS as described above or as obtainable by the above described method for use as a medicament. The medicament can be applied for the treatment of any condition, which is alleviated or cured by the application of a tetrahydrocannabinol, however, in this respect the treatment of nausea, vomiting, neuropathic pain, fibromyalgia, anorexia, cachexia, multiple sclerosis, traumatic cross-sectional disorders, dystonic movement disorders, asthma bronchiale, epileptic seizures, withdrawal symptoms in alcohol, benzodiazepine and opiate addiction, Parkinson's disease, dementia, Alzheimer's disease, arthritis, glaucoma, migraine, dysmenorrhea or Tourette syndrome is preferred.

Thus, in a yet further aspect, the present invention relates to a TTS as described above and as obtainable by the above described method for use in the treatment of nausea, vomiting, neuropathic pain, fibromyalgia, anorexia, cachexia, multiple sclerosis, traumatic cross-sectional disorders, dystonic movement disorders, asthma bronchiale, epileptic seizures, withdrawal symptoms in alcohol, benzodiazepine and opiate addiction, Parkinson's disease, dementia, Alzheimer's disease, arthritis, glaucoma, migraine, dysmenorrhea or Tourette syndrome.

Preferably, said TTS is for use in the treatment of neuropathic pain, fibromyalgia and/or Tourette syndrome.

The present invention is explained in the following Examples, which are presented for illustrative purposes only and should not be taken as limiting in any regard.

EXAMPLE: TETRAHYDROCANNABINOL BASED TRANSDERMAL THERAPEUTIC SYSTEMS

Transdermal therapeutic systems Thc0103, Thc104, Thc105, Thc0109, Thc0112, Thc0114, according to the present invention were prepared using only the adhesive layer as a reference system. The constituents and amounts of the adhesive layer are indicated in the following Table 1.

TABLE 1

| | | Adhesive layer composition [%] | | | | | | Area |
|---|---|---|---|---|---|---|---|---|
| Formulation | Active agent | Polysiloxane polymer | | Solubilizer | | Permeation enhancer | Antioxidant | weight [g/m²] |
| Thc0103 | THC 8 | Bio-PSA 4301 58.73 | Bio-PSA 4201 25.17 | PVP 30 8 | | | Tocopherol 0.1 | 164 |
| Thc0104 | THC 8 | Bio-PSA 4301 58.73 | Bio-PSA 4201 25.17 | Labrafil ® M 1944 CS 8 | | | Tocopherol 0.1 | 157 |
| Thc0105 | THC 8 | Bio-PSA 4301 58.73 | Bio-PSA 4201 25.17 | Lauric acid 2 | | Propylene glycol 6 | Tocopherol 0.1 | 151 |
| Thc0109 | THC 8 | Bio-PSA 4301 70 | Bio-PSA 4201 30 | Caprylic acid 6 | | Propylene glycol 2 | Tocopherol 0.1 | |
| Thc0112 | THC 8 | Bio-PSA 4301 58.73 | Bio-PSA 4201 25.17 | Lauric acid 4 | PVP 30 1 | Propylene glycol 3 | Tocopherol 0.1 | 155 |
| Thc0114 | THC 8 | Bio-PSA 4301 58.73 | Bio-PSA 4201 25.17 | Brij L4 4 | | Transcutol 4 | Tocopherol 0.1 | 149 |

THC: Tetrahydrocannabinol
Transcutol: 2-(2-ethoxyethoxy)ethanol
Brij L4: polyethylene glycol dodecyl ether/polyoxyethylene(4)lauryl ether
PVP 30: polyvinylpyrrolidone 30
Labrafil ® M 1944 CS: PEG-6 mono- and diesters of oleic acid in admixture with mono-, di- and triglycerides

The in vitro human skin permeation of the systems listed in Example 1 was measured by use of a Franz cell. For the measurement, the adhesive layer was applied to the skin (400 μm of dermatomized skin) in the donor compartment. The acceptor compartment is filled with buffer or other solutions. By regular sampling from the acceptor compartment, the permeation of the substance over the selected period is followed through the skin. The influence of penetration enhancers on the permeation of a substance is also tested by means of this system. The use of the Franz cell as a diffusion model is primarily suitable for predicting the transport of drugs through human skin (=permeation), which corresponds to systemic availability.

In this case, 400 μm of dermatomized skin with a diffusion area of about 1,191 cm$^2$ were incubated with the topical therapeutic system. An aqueous isotonic phosphate buffer pH=5.5 plus 0.1% Na-azide, 1% Tween 20. 1% ascorbic acid and plus 0.1% 2-Hydroxypropyl-ß-Cyclodextrin with a filling volume of 10 mL served as the acceptor medium. The measurement of the permeation was carried out at a temperature of 32° C. and measured after 8, 24, 32, 48, 56, 72, 80, 144, 152 and 168 hours (n=3).

Figure 2:
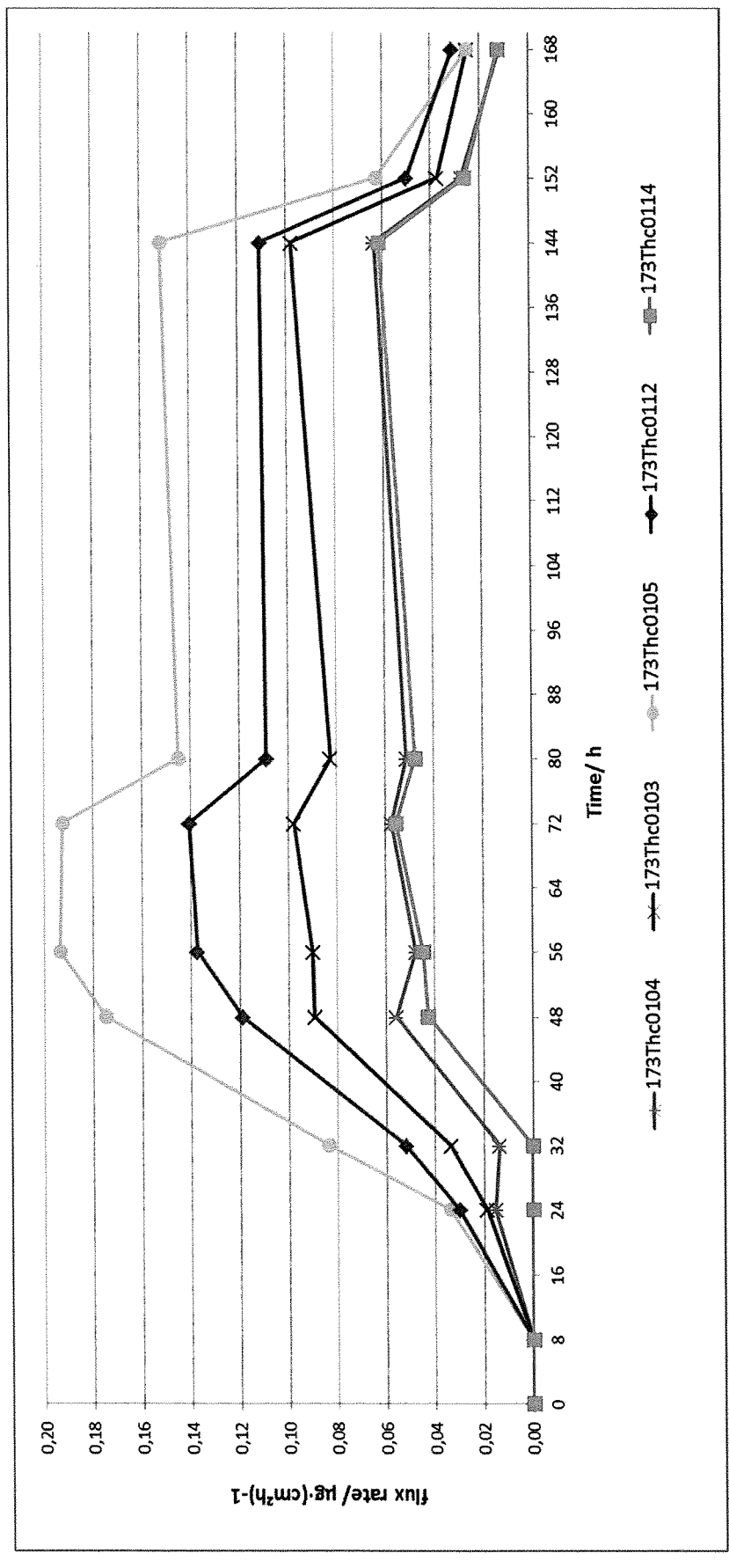
FIG. 2 is the graphical representation of human skin permeation flux rate after 168 hours.

From this data, the cumulated permeated active agent after 168 h (see FIG. 1) as well as the human skin permeation flux rate after 168 hours (see FIG. 2) were determined. Moreover, the residual amount of active agent in the skin as well as the utilization of the active agent was calculated. Finally, the TTS was visually inspected for its color and the adhesion and cohesion was haptically tested. The results are summarized in Table 2.

10 amine-resistant, and wherein the adhesive layer comprises a mixture of a high-tack and a medium or low-tack silicone polymer.

2. Transdermal therapeutic system according to claim 1, wherein the polysiloxane is self-adhesive.

3. Transdermal therapeutic system according to claim 1, wherein the at least one tetrahydrocannabinol is selected from Δ8-tetrahydrocannabinol, Δ9-tetrahydrocannabinol and R-(6a,10a)-Δ9-tetrahydrocannabinol.

4. Transdermal therapeutic system according to claim 1, wherein the at least one tetrahydrocannabinol is present in an amount from 0.1 to 20% by weight based on the total weight of the at least one adhesive layer.

5. Transdermal therapeutic system according to claim 1, wherein C2 to C20 saturated or unsaturated aliphatic carboxylic acids are excluded as solubilizer.

6. Transdermal therapeutic system according to claim 1, wherein the at least one solubilizer is present in an amount from 0.1 to 12% by weight based on the total weight of the at least one adhesive layer.

7. Transdermal therapeutic system according to claim 1, further comprising at least one permeation enhancer.

8. Transdermal therapeutic system according to claim 6, wherein the at least one permeation enhancer is selected from the group consisting of PEG-6 apricot kernel oil, propylene glycol, 2-(2-ethoxyethoxy)ethanol.

9. Transdermal therapeutic system according to claim 1, wherein the transdermal therapeutic system does not contain a compound having an HLB of 6 or more.

TABLE 2

| Formulation | cumulated permeated active agent after 168 h [μg/cm$^2$] | Residual amount of active agent in the skin [μg/cm$^2$] | Flux rate after 168 h [μg/cm$^2$ × h] | Utilization of the active agent [%] | Visual inspection | Adhesion/Cohesion |
|---|---|---|---|---|---|---|
| Thc0103 | 12 | 6.2 | | 0.03 | light yellowish | +/+ |
| Thc0104 | 8 | 39.2 | | 0.01 | whitish | +/+ |
| Thc0105 | 20 | 15.2 | | 0.02 | light yellowish | +/+ |
| Thc0109 | 140 | | 1.51 | | | +/+ |
| Thc0112 | 15 | 7 | | 0.03 | whitish | +/+ |
| Thc0114 | 7 | 11.3 | | 0.01 | light yellowish | +/+ |

For the formulations Thc0105, Thc0112 and Thc0114 particularly favorable characteristics of no observable skin irritation, no cohesive failure during wear and no remaining sticky residues on removal of the patch were detected.

The invention claimed is:

1. A transdermal therapeutic system comprising
i) an active agent impermeable backing layer, ii) at least one adhesive layer comprising at least 70% by weight of at least two polysiloxane polymer, at least one tetrahydrocannabinol (THC) and at least one solubilizer, and optionally iii) a protective layer for removal before use, wherein the at least one solubilizer is selected from the group consisting of polyvinylpyrrolidone, pentanoic acid, capric acid, caprylic acid, myristic acid, palmitic acid, stearic acid, arachidic acid, behenic acid, linoleic acid, lignoceric acid, isoverlic acid, neoheptonic acid, neonanonic acid, isostearic acid, pentanoic acid, hexanoic acid, ricinoleic acid, octanoic acid, nonanoic acid, decanoic acid, lauric acid, oleic acid, arachidonic acid, galloleic acid, erucic acid, polyethylene glycol monolaureate, PEG-6 mono- and diesters of oleic acid, polyethylene glycol dodecyl ether/polyoxyethylene(4)lauryl ether, a polyvinylcaprolactam-/polyvinylacetate-/polyethyleneglycol-co-polymer, wherein the polysiloxane polymers are

10. Transdermal therapeutic system according to claim 1, further comprising at least one antioxidant.

11. A method for preparing a transdermal therapeutic system according to claim 1, comprising the steps of:
a) preparing a mixture comprising at least two polysiloxane polymer, at least one tetrahydrocannabinol and at least one solubilizer;
b) applying the mixture of a) on a protective layer for removal before use, and
c) applying an active agent impermeable backing layer on the layer of the mixture prepared in step b).

12. Transdermal therapeutic system according to claim 1 for use as a medicament.

13. Transdermal therapeutic system according to claim 10, wherein the at least one antioxidant comprises tocopherol, ascorbyl palmiate, ascorbic acid, butylhydroxytoluol, or a combination of thereof.

14. Transdermal therapeutic system according to claim 12, wherein the medicament is effective in the treatment of nausea, vomiting, neuropathic pain, fibromyalgia, anorexia, cachexia, multiple sclerosis, traumatic cross-sectional disorders, dystonic movement disorders, asthma bronchiale, epileptic seizures, withdrawal symptoms in alcohol, benzodiazepine and opiate addiction, Parkinson's disease, dementia, Alzheimer's disease, arthritis, glaucoma, migraine, dysmenorrhea or Tourette syndrome.

15. A transdermal therapeutic system comprising
i) an active agent impermeable backing layer, ii) at least one adhesive layer comprising at least 70% by weight of at least two polysiloxane polymer, at least one tetrahydrocannabinol (THC) and at least one solubilizer, and iii) a protective layer for removal before use, wherein the at least one solubilizer is selected from the group consisting of polyvinylpyrrolidone, pentanoic acid, capric acid, caprylic acid, myristic acid, palmitic acid, stearic acid, arachidic acid, behenic acid, linoleic acid, lignoceric acid, isoverlic acid, neoheptonic acid, neonanonic acid, isostearic acid, pentanoic acid, hexanoic acid, ricinoleic acid, octanoic acid, nonanoic acid, decanoic acid, lauric acid, oleic acid, arachidonic acid, galloleic acid, erucic acid, polyethylene glycol monolaureate, PEG-6 mono- and diesters of oleic acid, polyethylene glycol dodecyl ether/polyoxyethylene(4) lauryl ether, a polyvinylcaprolactam-/polyvinylacetate-/polyethyleneglycol-copolymer, wherein the polysiloxane polymers are amine-resistant, and wherein the adhesive layer comprises a mixture of a high-tack and a medium or low-tack silicone polymer.

\*    \*    \*    \*    \*